United States Patent
Makino

(10) Patent No.: US 11,363,177 B2
(45) Date of Patent: Jun. 14, 2022

(54) ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 17/260,397

(22) PCT Filed: Feb. 26, 2020

(86) PCT No.: PCT/JP2020/007866
§ 371 (c)(1),
(2) Date: Jan. 14, 2021

(87) PCT Pub. No.: WO2020/189213
PCT Pub. Date: Sep. 24, 2020

(65) Prior Publication Data
US 2021/0266434 A1   Aug. 26, 2021

(30) Foreign Application Priority Data

Mar. 20, 2019 (JP) .............................. JP2019-053829

(51) Int. Cl.
*H04N 5/225* (2006.01)
*G06T 7/50* (2017.01)
*G06T 7/90* (2017.01)

(52) U.S. Cl.
CPC ............. *H04N 5/2254* (2013.01); *G06T 7/50* (2017.01); *G06T 7/90* (2017.01);
(Continued)

(58) Field of Classification Search
CPC . G06T 2207/10024; G06T 2207/10068; G06T 2207/30096; G06T 2207/30101;
(Continued)

(56) References Cited

U.S. PATENT DOCUMENTS

| 2012/0121144 A1 | 5/2012 | Tanaka |
| 2015/0356369 A1 | 12/2015 | Kitamura et al. |
| 2016/0089011 A1* | 3/2016 | Shiraishi .............. A61B 1/0684 348/71 |

FOREIGN PATENT DOCUMENTS

| JP | 2008-229157 | 10/2008 |
| JP | 2014-161672 | 9/2014 |

(Continued)

OTHER PUBLICATIONS

Kuri, K. S. et al., "Automated retinal blood vessels extraction using optimized Gabor filter", 2014 International Conference on Informatics, Electronics & Vision, May 24, 2014.*

(Continued)

*Primary Examiner* — Dakshesh D Parikh
(74) *Attorney, Agent, or Firm* — Greenblum & Bernstein, P.L.C.

(57) ABSTRACT

An endoscope system processor includes: a blood vessel region determination unit that obtains a likelihood of a blood vessel region by a numerical value on the basis of a shape characterizing a blood vessel in each of a plurality of parts of an image of a biological tissue, from the image obtained by an electronic endoscope; and a blood vessel feature amount calculation unit that calculates a blood vessel feature amount indicating a feature amount of the blood vessel region by integrating the numerical values of the likelihood of the blood vessel region with each other in the entire image. The blood vessel region determination unit calculates an approximation degree as the likelihood of the blood vessel region, using a spatial filter.

8 Claims, 9 Drawing Sheets

(52) U.S. Cl.
    CPC ............ *G06T 2207/10024* (2013.01); *G06T 2207/10068* (2013.01); *G06T 2207/30096* (2013.01); *G06T 2207/30101* (2013.01); *H04N 2005/2255* (2013.01)

(58) Field of Classification Search
    CPC .......... G06T 7/0012; G06T 7/50; G06T 7/90; H04N 2005/2255; H04N 5/2254; H04N 5/2256; G06V 10/255; G06V 10/56; G06V 2201/03; A61B 1/00009
    See application file for complete search history.

(56) References Cited

FOREIGN PATENT DOCUMENTS

| | | |
|---|---|---|
| JP | 2016-67778 | 5/2016 |
| WO | 2012/011303 | 1/2012 |

OTHER PUBLICATIONS

Kuri, K. S. et al., "Automated retinal blood vessels extraction using optimized Gabor filter", 2014 International Conference on Informatics, Electronics & Vision, May 24, 2014, 5 pages.

Kanno, Ryota et. al., "Extracting blood vessel parameters on image of large intestine endoscope", IEICE Technical Report, Jul. 2, 2010, pp. 7-11, with translation.

Kuri, K. S., "Automatic diabetic retinopathy detection using OMFR with minimum cross entropy threshold", 2015 International Conference on Electrical Engineering and Information Communication Technology, May 23, 2015, 6 pages.

Official Communication issued in International Bureau of WIPO Patent Application No. PCT/JP2020/007866, dated May 26, 2020.

\* cited by examiner

ENDOSCOPE SYSTEM

TECHNICAL FIELD

The present invention relates to an endoscope system that processes an image of a biological tissue in a body cavity.

BACKGROUND ART

A lesion part in a biological tissue has various levels of severity, from an inflammation in which a mucosal layer of the biological tissue becomes thin, such that the biological tissue becomes rough to exhibit a red color, to an ulcer that the mucosal layer and its lower layer are partially missing. The lesion part, for example, an inflammatory part generally exhibits a red color different from that of a normal mucosal tissue. It has also become possible to identify a lesion part such as an inflammatory part or the like having a color slightly different from that of a normal tissue, due to improvement in the performance of a color endoscope device. However, images of blood vessels exhibiting a red color also appear in or near the inflammatory part exhibiting the red color. For this reason, a degree of an inflammation in the inflammatory part cannot be accurately evaluated only by a strength of a component of the red color. For this reason, it is necessary to perform evaluation regarding the blood vessels.

In addition, evaluating the number of blood vessels appearing in a biological tissue regardless of the lesion part, as well as the blood vessels existing in or near the inflammatory part is used to evaluate a health condition of the biological tissue, and desirable to judge a transition to the lesion part in advance.

For example, image processing capable of improving detection accuracy of a blood vessel from a captured image of a biological tissue has been proposed (Patent Literature 1).

In the above image processing, a blood vessel candidate region in which it is estimated that a shape structure of the blood vessel exists is detected, a difference between feature amounts of outer and inner sides of each of neighboring regions on both sides of the detected blood vessel candidate region is calculated, and a detection result of the blood vessel candidate region is corrected on the basis of this difference.

It has been mentioned that detection accuracy of the blood vessel is improved as a result.

CITATION LIST

Patent Literature

Patent Literature 1: WO 2012/011303

SUMMARY OF INVENTION

Technical Problem

However, some of the blood vessels are thick and some of the blood vessels are thin, and an image of the biological tissue may be captured at a position close to the biological tissue or be captured from a position distant from the biological tissue, such that thicknesses of the images of blood vessels appearing in the image also change greatly. Therefore, it is difficult to appropriately detect images of blood vessels having different thicknesses in the image as the blood vessel candidate region or appropriately detect an image of a blood vessel whose thickness changes for each image in spite of the same blood vessel due to different visual field ranges as a blood vessel candidate region. Patent Literature 1 disclosing a method of detecting the blood vessel candidate region does not disclose a method of appropriately detecting the images of the blood vessels having the different thicknesses in the image as the blood vessel candidate region or a method of appropriately detecting the image of the blood vessel whose thickness changes for each image in spite of the same blood vessel as the blood vessel candidate region.

Therefore, an object of the present invention is to provide an endoscope system capable of appropriately determining a blood vessel region in an image of a biological tissue regardless of a thickness of a blood vessel in the image.

Solution to Problem

An aspect of the present invention is an endoscope system. The endoscope system includes:

an electronic endoscope configured to capture an image of a biological tissue; and a processor that includes an image processing unit including: a blood vessel region determination unit configured to obtain a likelihood of a blood vessel region appearing in the image of the biological tissue as a numerical value on the basis of a shape characterizing a blood vessel, for each of a plurality of parts of the image of the biological tissue, from the image of the biological tissue obtained by the electronic endoscope; and a blood vessel feature amount calculation unit configured to calculate a blood vessel feature amount indicating a feature amount of the blood vessel region by integrating the numerical values of the likelihood of the blood vessel region with each other in the entire image.

The blood vessel region determination unit is configured to calculate an approximation degree as the likelihood of the blood vessel region, for each pixel of the image, using a spatial filter with respect to a pixel row of at least one stage of the image extracted along one direction of array directions of pixels of the image, the approximation degree representing a degree of approximation to a pattern shape that approximates to a blood vessel shape, by a numerical value, and the spatial filter being composed of a plurality of pixels whose pixel values are represented so as to correspond to the pattern shape.

A size of the spatial filter along the one direction is larger than that of the spatial filter along an orthogonal direction orthogonal to the one direction.

The blood vessel region determination unit may associate pixels of an examination target area of the pixel row with respective pixels of the spatial filter, and obtain the approximation degree on the basis of a total value of values obtained by multiplying pixel values of the pixels of the examination target area by pixel values of corresponding pixels of the spatial filter.

The spatial filter may be provided so as to correspond to each of a plurality of pattern shapes, and the blood vessel region determination unit may be configured to calculate a maximum value of a plurality of approximation degrees obtained using the spatial filter corresponding to each of the plurality of pattern shapes as the likelihood of the blood vessel region.

The plurality of pattern shapes may include a linear shape extending in the orthogonal direction and an inclined shape extending at an inclination angle exceeding 0° and less than 90° with respect to the orthogonal direction.

A ratio of a dimension of the spatial filter in the one direction to a dimension of the spatial filter in the orthogonal direction may be 20 to 100.

An image of the biological tissue used at the time of obtaining the likelihood of the blood vessel region of the biological tissue may be a color component image in which information regarding an amount of a predetermined color component in the image of the biological tissue obtained by the electronic endoscope is represented by a numerical value for each pixel.

The image processing unit may include:

a pixel evaluation value calculation unit including: a color component calculation unit configured to calculate a first pixel evaluation value for each pixel, the first pixel evaluation value being a pixel evaluation value capable of distinguishing a feature of an appearance appearing in a lesion part of the biological tissue from a feature of an appearance of a healthy part of the biological tissue by a color component indicated by the lesion part and indicating a degree of the feature regarding the color component indicated by the lesion part; and the blood vessel region determination unit, the blood vessel region determination unit may be configured to calculate a second pixel evaluation value, for each pixel, using a color component image configured with the first pixel evaluation value calculated by the color component calculation unit as a pixel value as an image for obtaining the numerical value of the likelihood of the blood vessel region, the second pixel evaluation value representing the likelihood of the blood vessel region by a numerical value, and the image processing unit may further include:

a representative value calculation unit including: the blood vessel feature amount calculation unit configured to calculate the blood vessel feature amount as a second representative evaluation value in the blood vessel region by integrating the second pixel evaluation values with each other in the entire color component image, the second pixel evaluation values being numerical values of the likelihood of the blood vessel region; and a biological tissue feature amount calculation unit configured to calculate a first representative evaluation value of the feature of the biological tissue by integrating the first pixel evaluation values of each pixel in the color component image with each other; and an integration unit configured to calculate one numerical value obtained by calculating and integrating the first representative evaluation value and the second representative evaluation value with each other, as a severity of a lesion of the lesion part.

A degree of the feature of the appearance may be a degree of inflammation of the biological tissue, and the color component may be a red component.

The color component of the image may include a red component, a green component, and a blue component, and the color component calculation unit may be configured to calculate the first pixel evaluation value on the basis of a deviation angle at which a direction of a line segment connecting a reference point set in a color space and a pixel corresponding point corresponding to a color component of each pixel of the image to each other deviates from a predetermined reference axis passing through the reference point, the color space being defined by the red component and the blue component or the green component.

Advantageous Effects of Invention

According to the endoscope system described above, the blood vessel region can be appropriately determined regardless of a thickness of a blood vessel in the image.

DESCRIPTION OF EMBODIMENTS

In order to appropriately determine a blood vessel region of an image of a blood vessel in a captured image of a biological tissue regardless of a thickness of the image of the blood vessel, in an endoscope system according to the present disclosure, a blood vessel region determination unit configured to obtain a likelihood of the blood vessel region appearing in the image of the biological tissue on the basis of a shape characterizing the blood vessel, for each of a plurality of parts of the image of the biological tissue from the image of the biological tissue obtained by an electronic endoscope is provided in a processor. The blood vessel region determination unit is configured to calculate an approximation degree as the likelihood of the blood vessel region, for each pixel of the image, using a spatial filter with respect to a pixel row or pixel rows of one stage or two or more stages of an image extracted along one direction of array directions of pixels of the image, the spatial filter corresponding to a pattern shape (for example, a line shape) that approximates to a blood vessel shape, and the approximation degree representing a degree of approximation to the pattern shape by a numerical value. The spatial filter is a filter composed of N pixels×M pixels (N and M are natural numbers of 2 or more) whose pixel values are represented so as to correspond to the pattern shape that approximates to the blood vessel shape. A size of the spatial filter along the one direction is larger than that of the spatial filter along an orthogonal direction orthogonal to the one direction.

Since the spatial filter has an elongated shape by making a size of N pixels×M pixels in the spatial filter along the one direction larger than a size thereof along the orthogonal direction orthogonal to the one direction as described above, even though the thickness of the image of the blood vessel is large, the size of the spatial filter along the one direction is long, and the spatial filter can thus be arranged so as to straddle edges of both sides of the image of the blood vessel. Conventionally, in a case where the image of the blood vessel is thick, the spatial filter was arranged inside the image of the blood vessel, and thus, could not straddle the edges of both sides, such that the likelihood of the blood vessel region has been reduced. In the present disclosure in which the spatial filter is arranged so as to straddle the edges of both sides of the image of the blood vessel even though the image of the blood vessel is thick as described above, the blood vessel region can be appropriately determined regardless of the thickness of the blood vessel in the image.

Hereinafter, an endoscope system according to an embodiment will be specifically described with reference to the drawings.

Figure 1:
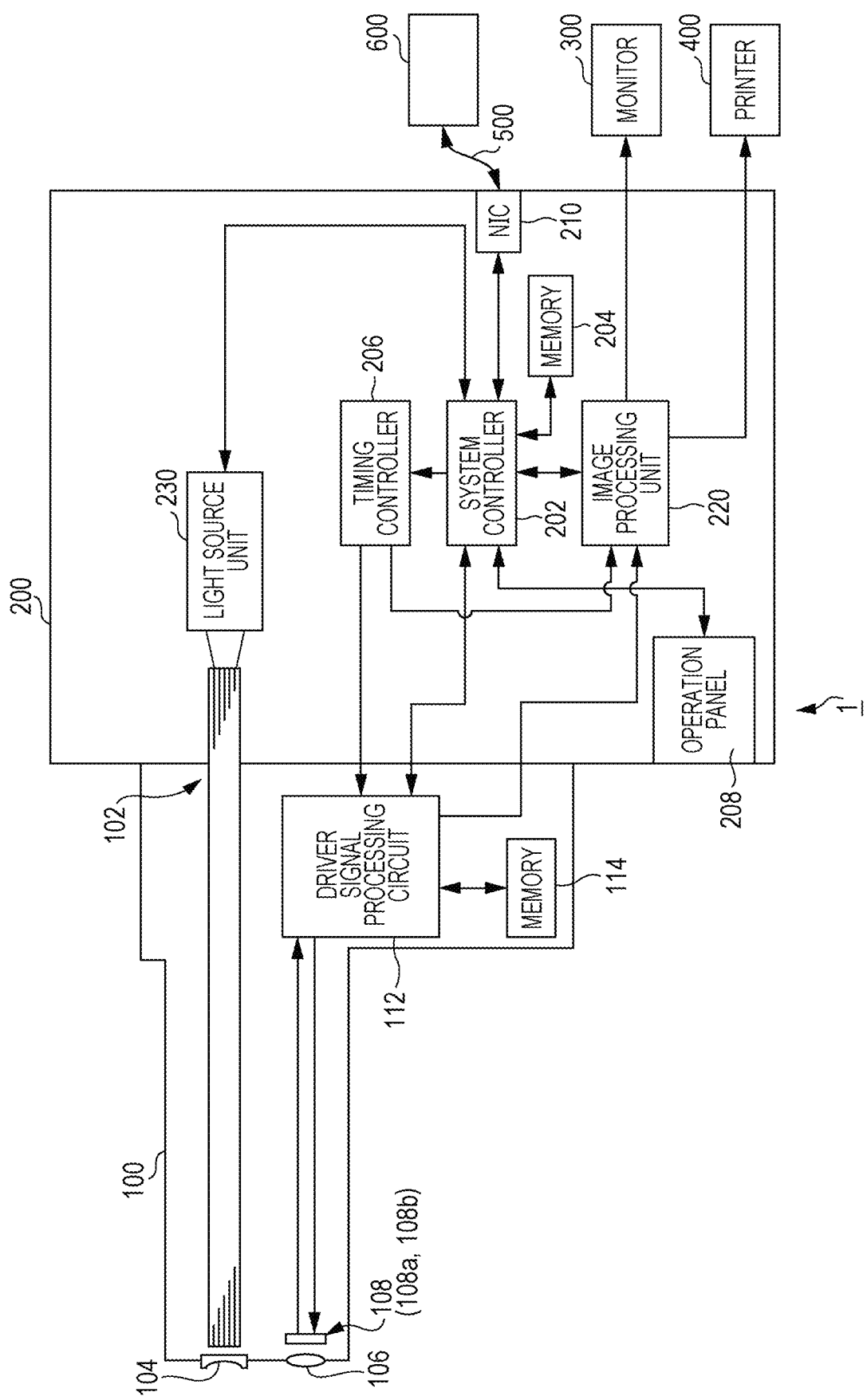
FIG. 1 is a block diagram illustrating a configuration of an endoscope system according to an embodiment.

FIG. 1 is a block diagram illustrating a configuration of an electronic endoscope system 1 according to an embodiment.

As illustrated in FIG. 1, the electronic endoscope system 1 includes an electronic endoscope 100, a processor 200 for an electronic endoscope, a monitor 300, and a printer 400.

The processor 200 for an electronic endoscope includes a system controller 202 or a timing controller 206. The system controller 202 executes various programs stored in a memory 204, and integrally controls the entire electronic endoscope system 1. In addition, the system controller 202 changes various settings of the electronic endoscope system 1 according to an instruction by a user (an operator or an assistant) input to an operation panel 208. The timing controller 206 outputs a clock pulse for adjusting an operation timing of each unit to each circuit in the electronic endoscope system 1.

The processor 200 for an electronic endoscope includes a light source unit 230 that supplies illumination light to the electronic endoscope 100. The light source unit 230 includes, for example, a high-luminance lamp that emits white illumination light by receiving drive power supplied from a lamp power source, for example, a xenon lamp, a metal halide lamp, a mercury lamp, or a halogen lamp, although not illustrated. The light source unit 230 is configured so that the illumination light emitted from the high-luminance lamp is condensed by a condensing lens (not illustrated) and then incident on an incident end of a light carrying bundle (LCB) 102, which is a bundle of optical fibers of the electronic endoscope 100, via a dimmer (not illustrated).

Alternatively, the light source unit 230 includes a plurality of light emitting diodes that emit light in a wavelength band of a predetermined color. The light source unit 230 is configured so that light emitted from the light emitting diodes is synthesized using an optical element such as a dichroic mirror or the like and the synthesized light is condensed as illumination light by a condenser lens (not illustrated), and then incident on an incident end of light carrying bundle (LCB) 102 of the electronic endoscope 100.

A laser diode can be used instead of the light emitting diode. The light emitting diode and the laser diode have features such as low power consumption, a low heat generation amount, and the like, as compared with other light sources, and thus, have an advantage that a bright image can be acquired while suppressing power consumption or a heat generation amount.

In an example illustrated in FIG. 1, the light source unit 230 is built in the processor 200 for an electronic endoscope, but may be provided in the electronic endoscope system 1 as a device separate from the processor 200 for an electronic endoscope. In addition, the light source unit 230 may be provided at a distal tip of an electronic endoscope 100 to be described later. In this case, the LCB 102 that guides the illumination light is not required.

The illumination light incident from the incident end into the LCB 102 is propagated in the LCB 102 and is emitted from an emission end of the LCB 102 arranged in the distal tip of the electronic endoscope 100, and is applied to an object via a light distribution lens 104. Reflected light from the object forms an optical image on a light receiving surface of a solid-state image sensor 108 via an objective lens 106.

The solid-state image sensor 108 is, for example, a single-plate color charge-coupled device (CCD) image sensor in which various filters of an infrared (IR) cut filter 108a and a Bayer array color filter 108b are arranged on a light receiving surface, and generates each primary color signal of red (R), green (G), and blue (B) according to an optical image formed on the light receiving surface. A single-plate color complementary metal oxide semiconductor (CMOS) image sensor can also be used instead of the single-plate color CCD image sensor. An image of the CMOS image sensor generally tends to be generally darker than that of the CCD image sensor. Therefore, in digitization processing for performing evaluation of a degree of inflammation described below, an advantageous effect that a fluctuation of an inflammation evaluation value due to brightness of the image can be suppressed is more remarkable in a case of using the CMOS image sensor.

A driver signal processing circuit 112 is provided in a connector unit of the electronic endoscope 100 connected to the processor 200 for an electronic endoscope. The driver signal processing circuit 112 generates an image signal (a luminance signal Y and color difference signals Cb and Cr) by performing predetermined signal processing such as color interpolation, matrix calculation, or the like on the primary color signal input from the solid-state image sensor 108, and outputs the generated image signal to an image processing unit 220 of the processor 200 for an electronic endoscope. In addition, the driver signal processing circuit 112 accesses a memory 114 to read device-specific information of the electronic endoscope 100. The device-specific information of the electronic endoscope 100 recorded in the memory 114 includes, for example, the number of pixels or sensitivity of the solid-state image sensor 108, an operable frame rate, a model number, or the like. The driver signal processing circuit 112 outputs the device-specific information read from the memory 114 to the system controller 202. As described above, the electronic endoscope 100 captures an image of the biological tissue in a body cavity using the solid-state image sensor 108.

The system controller 202 performs various calculations on the basis of the device-specific information of the electronic endoscope 100 and generates a control signal. The system controller 202 controls operations and timings of various circuits in the processor 200 for an electronic endoscope using the generated control signal so as to perform processing suitable for the electronic endoscope 100 connected to the processor 200 for an electronic endoscope.

The timing controller 206 supplies a clock pulse to the driver signal processing circuit 112, the image processing unit 220, and the light source unit 230 in accordance with timing control by the system controller 202. The driver signal processing circuit 112 performs driving control of the solid-state image sensor 108 at a timing synchronized with a frame rate of a video processed on the processor 200 for an electronic endoscope side in accordance with the clock pulse supplied from the timing controller 206.

The image processing unit 220 generates a video signal for displaying an endoscope image or the like on the monitor on the basis of the image signal input from the driver signal processing circuit 112 and outputs the video signal to the monitor 300, under the control of the system controller 202. Further, the image processing unit 220 performs digitization processing to be described later on the image of the biological tissue obtained by the electronic endoscope 100, obtains an inflammation evaluation value that digitizes and indicates a degree of inflammation of the biological tissue on the basis of information of color components of the image, and generates a color map image in which the pixel evaluation values of each pixel obtained by the digitization processing are replaced with colors. Specifically, the image processing unit 220 generates a video signal for displaying information of the inflammation evaluation value and the color map image on the monitor, and outputs the video signal to the monitor 300. Therefore, the operator can accurately perform, for example, evaluation of a degree of inflammation of a biological tissue to which he/she pays attention through the image displayed on a display screen of the monitor 300. The image processing unit 220 outputs the inflammation evaluation value and the color map image to the printer 400, if necessary.

The processor 200 for an electronic endoscope is connected to a server 600 via a network interface card (NIC) 210 and a network 500. The processor 200 for an electronic endoscope can download information (for example, electronic medical record information of a patient or information of the operator) regarding an endoscopic examination from the server 600. The downloaded information is displayed, for example, on the display screen of the monitor 300 or the operation panel 208. In addition, the processor 200 for an electronic endoscope can save endoscopic examination results (endoscope image data, examination conditions, an image analysis result, an operator's opinion, and the like) in the server 600 by uploading the endoscopic examination results to the server 600.

First Embodiment

Figure 2:
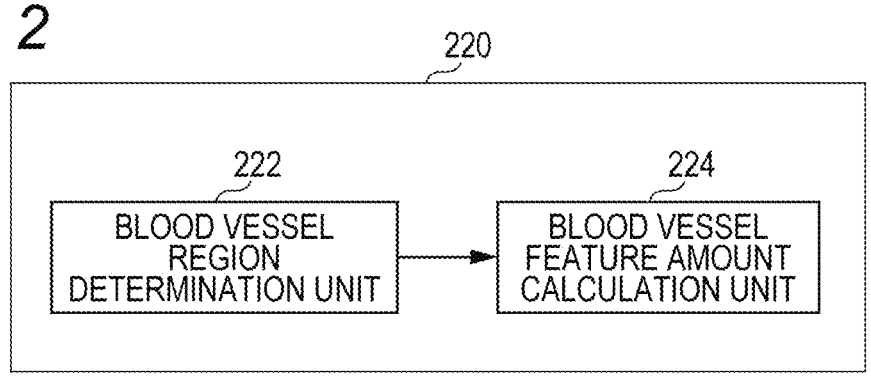
FIG. 2 is a diagram illustrating an example of a configuration of an image processing unit that obtains a likelihood of a blood vessel region in a first embodiment.

FIG. 2 is a diagram illustrating an example of main units of a configuration of the image processing unit 220 that obtains a likelihood of a blood vessel region in a first embodiment.

The image processing unit 220 includes a blood vessel region determination unit 222 and a blood vessel feature amount calculation unit 224.

The blood vessel region determination unit 222 is configured to obtain a likelihood of a blood vessel region in the image as a numerical value on the basis of a shape characterizing a blood vessel for each of a plurality of parts of the image of the biological tissue from the image of the biological tissue obtained by the electronic endoscope.

The blood vessel feature amount calculation unit 224 is configured to calculate a blood vessel feature amount indicating a feature of the blood vessel by a numerical value by integrating the numerical values of the likelihood of the blood vessel region with each other in the entire image.

Here, the blood vessel region determination unit 222 is configured to calculate an approximation degree representing a degree of approximation to a pattern shape by a numerical value, as the likelihood of the blood vessel region, using a spatial filter composed of a plurality of pixels whose pixel values are represented so as to correspond to the pattern shape that approximates to a blood vessel shape, with respect to a pixel row of at least one stage of an image extracted along one direction of array directions of pixels of the image. The approximation degree is calculated for each pixel of the image. Hereinafter, the spatial filter is also referred to as a template.

The likelihood of the blood vessel region is determined using the template TP. The template (spatial filter) TP has a rectangular shape having values corresponding to white regions and gray regions illustrated in FIGS. 5(a) to 5(e) to be described later for each pixel. Therefore, according to the embodiment, the likelihood (approximation degree) of the blood vessel region is a correlation coefficient between pixel values of the template TP and corresponding pixel values of a determination target area by the template TP. In addition, according to the embodiment, the likelihood (approximation degree) of the blood vessel region may be a total value of values obtained by using pixel values for each pixel of the template TP as filter coefficients and multiplying each of the filter coefficients by corresponding pixel values of the determination target area.

The blood vessel region determination unit 222 gives such a correlation coefficient or total value to a pixel existing at the center of the template TP as a value of the likelihood of the blood vessel region.

Figure 3:
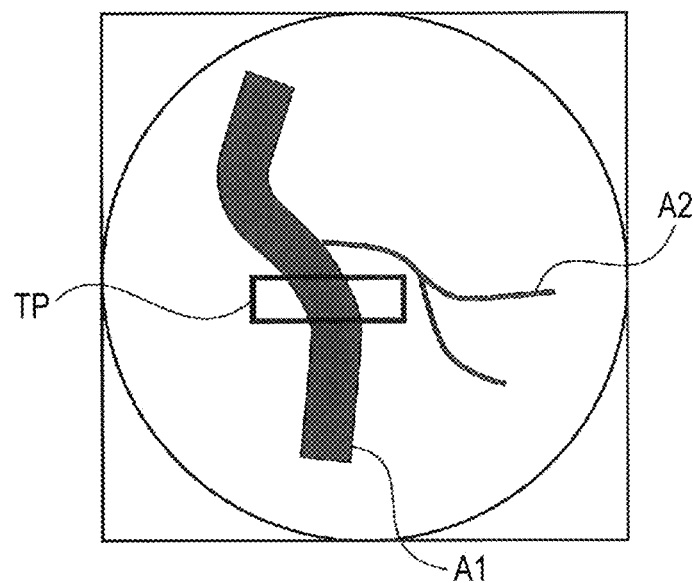
FIG. 3 is a diagram for describing an example in which a template (spatial filter) used in the first embodiment and a second embodiment is applied to an image in which a biological tissue is an object.

FIG. 3 is a diagram for describing an example in which the above template (spatial filter) is applied to an image in which the biological tissue is an object. In the image illustrated in FIG. 3, an image A1 of a thick blood vessel and an image A2 of a thin blood vessel are illustrated. The template TP used to calculate an approximation degree in FIG. 3 is represented by a rectangle. The template TP has a rectangular shape elongated in a horizontal direction in the example illustrated in FIG. 3. That is, the template TP has a shape in which a size of the template TP along one direction (a horizontal direction of a paper in FIG. 3) is larger than that of the template TP along an orthogonal direction (a vertical direction of the paper in FIG. 3) orthogonal to the one direction of the template. This is for the template TP to be able to detect the image A1 of the thick blood vessel by straddling edges of both sides of the image A1 of the thick blood vessel. Note that the use of the template TP elongated in the one direction as described above depends on a device configuration of the image processing unit 220. In many cases, the image processing unit 220 uses a line buffer that temporarily stores the pixel values of the pixel row of one stage of the image as a memory, for example, when it determines the likelihood of the blood vessel region using hardware such as a field-programmable gate array (FPGA) or the like. Since the pixel values of the pixel row of one stage along the one direction are read from this memory, determination processing can be simplified by using the template TP elongated along the one direction in response to this reading. In a case of reading pixel values of pixel arrays of two or more stages at the time of determining the likelihood of the blood vessel region, line buffers whose number corresponds to the number of stages are only required to be installed. In addition, since it is not necessary to secure a large memory capacity such as a frame memory, a configuration of the processor 200 for an electronic endoscope can be simplified. The number of line buffers in a case of using the template TP is smaller than the number of line buffers in a case of using a square template occupying the same number of pixels as that of the template TP.

Figure 4:
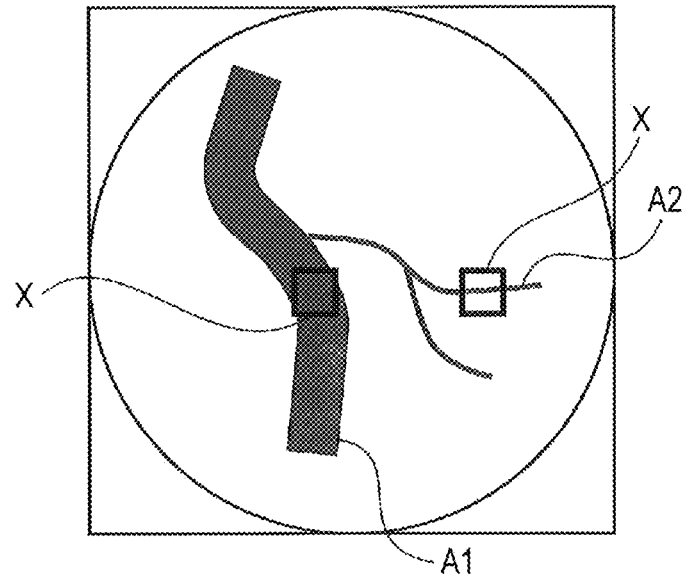
FIG. 4 is a diagram for describing an example in which a square template (spatial filter) is applied to an image in which a biological tissue is an object.

FIG. 4 is a diagram for describing an example in which a square template (spatial filter) X is applied to an image in which the biological tissue is an object. As illustrated in FIG. 4, since the template X straddles edges of both sides of an image A2 of a thin blood vessel, the template X can detect the image A2 of the thin blood vessel, but since the template X does not straddle edges of both sides of an image A1 of a thick blood vessel, the template X cannot detect the image A1 of the thick blood vessel.

FIGS. 5(a) to 5(e) are diagrams illustrating examples of templates (spatial filters) TP used in the embodiment. In FIGS. 5(a) to 5(e), templates TP whose size in a horizontal direction of a paper in FIGS. 5(a) to 5(e) is larger than that in a vertical direction of the paper are divided by lines corresponding to pixels. A dark gray region in FIGS. 5 (a) to 5 (e) indicates a pattern shape that approximates to a line shape of a blood vessel.

A template TP1 illustrated in FIG. 5(a) is a template corresponding to a pixel array of one stage. A pattern shape illustrated in FIG. 5(a) is a gray region in one pixel in a pixel row of one stage.

A template TP2 illustrated in FIG. 5(b) is a template corresponding to a pixel array of one stage. A pattern shape illustrated in FIG. 5(b) is a gray region in which three pixels in a pixel row of one stage are connected to each other in a horizontal direction of a paper.

A template TP3 illustrated in FIG. 5(c) is a template corresponding to a pixel array of three stages. A pattern shape illustrated in FIG. 5(c) is a gray region in which three pixels in pixel rows of three stages are connected to each other in a vertical direction of a paper and extend in the vertical direction of the paper.

A template TP4 illustrated in FIG. 5(d) is a template corresponding to a pixel array of three stages. A pattern shape illustrated in FIG. 5(d) is a gray region in which three pixels in pixel rows of three stages are connected to each other in a lower left-upper right direction of a paper and extend in a direction inclined with respect to a vertical direction of the paper.

A template TP5 illustrated in FIG. 5(e) is a template corresponding to a pixel array of three stages. A pattern shape illustrated in FIG. 5(e) is a gray region in which nine pixels in pixel rows of three stages are connected to each other in a vertical direction of a paper and extend in the vertical direction of the paper at a thickness of a three-pixel width.

The gray regions are set so that pixels existing at the centers of these gray regions coincide with pixels existing at the centers of each of the templates TP1 to TP5.

As described above, the number of stages of the pixel array in the template TP may be one stage or may be a plurality of stages such as two stages, three stages, and four stages. However, an amount of improvement in an effect of the determination of the likelihood of the blood vessel region by the template TP in accordance with the number of stages becomes small if the number of stages of the template TP exceeds 5. For this reason, considering the number of installed line buffers and complexity of the determination, the number of stages of the template TP is preferably 1 to 5 stages and more preferably 1 to 3 stages.

In the present embodiment, the template TP long in the one direction is used in order to reliably determine the likelihood of the blood vessel region even in the image of the thick blood vessel. In the electronic endoscope 100, since a visual field range in a captured image when the electronic endoscope is inserted into the body cavity is limited in advance, a maximum size of an image of the thickness of the blood vessel can also be obtained as schematic information depending on the limited visual field range. Therefore, a size of the template TP along the one direction can be set in advance according to the visual field range in the captured image. For this reason, it may not be necessary to prepare a plurality of templates TP having different sizes along the one direction and make repeated determinations using different templates TP.

Note that since the template TP long in the one direction is used, blood vessels that extend in parallel and linearly in the one direction cannot be appropriately determined. However, there are very few blood vessels that extend in parallel and linearly in the one direction in the biological tissue. For this reason, even though the template TP long in the one direction is used, an influence on a numerical value of the likelihood of the blood vessel region is small. In addition, since a blood vessel feature amount is calculated by integrating results of the likelihood of the blood vessel region with each other, an influence of inability to determine the blood vessels extending in parallel and linearly in the one direction on the blood vessel feature amount is very small.

It is preferable from the viewpoint of making an efficient determination of the likelihood of the blood vessel region that the number of pixels of the template TP along the one direction (the horizontal direction of the paper in FIGS. 5(a) to 5(e)) is 2% to 10% of the number of pixels, in the same direction, of the image used for determining the likelihood of the blood vessel region. In addition, it is preferable from the viewpoint of making an efficient determination of the likelihood of the blood vessel region that a ratio of a dimension (number of pixels) of the template TP in the one direction to a dimension (number of pixels) of the template TP in the orthogonal direction orthogonal to the one direction is 20 to 100.

In a case where spatial filters that have used the pixel values for each pixel of the templates TP1 to TP5 as the filter coefficients are used as the templates TP1 to TP5 illustrated in FIGS. 5(a) to 5(e), a total value of the filter coefficients is 0, pixels in the gray region are given a filter coefficient of a positive value (the same value in a case where the number of pixels in the gray region is plural), and pixels in the white region are given a filter coefficient of the same negative value.

For example, in the template TP2 illustrated in FIG. 5(b), in a case where the number of pixels of the template TP2 in the one direction (the horizontal direction of the paper illustrated in FIG. 5(b)) is 77, each of three pixels in the gray region is given a filter coefficient of value 74/3, and each of 74 pixels in the white region is given a filter coefficient of value −1. When the total value of the values obtained by multiplying each of the filter coefficients by the pixel values of the corresponding pixels in the determination target area is calculated as the approximation degree, in a case where all the pixel values in the determination target area are the same value, the approximation degree becomes zero. Meanwhile, in a case where an image of the blood vessel extending linearly is included in the determination target area, the approximation degree increases. It can be said that as the value of this approximation degree becomes larger, the image that approximates to the template TP is included. Therefore, the approximation degree is calculated for the template TP, and a calculation result is given to a center pixel of the determination target area as the likelihood of the blood vessel region. By using the above spatial filter as the template TP, it is possible to quickly determine the likelihood of the blood vessel region.

Figure 6:
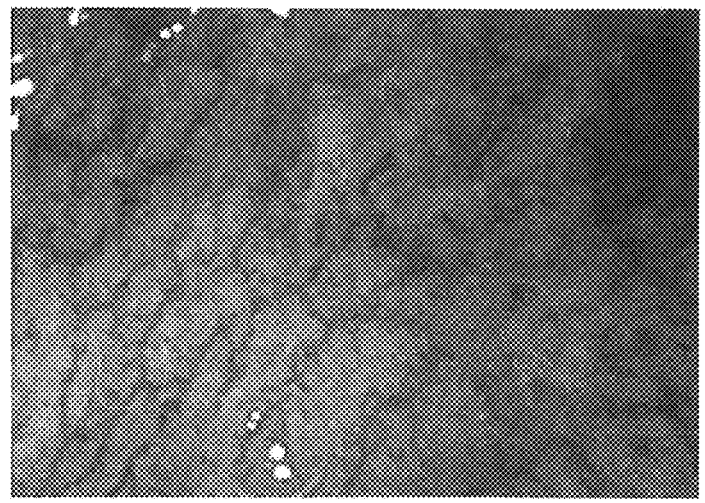
FIGS. 6(a) and 6(b) are diagrams illustrating an example of a captured image and a blood vessel extraction image obtained in the embodiment.
Figure 6:
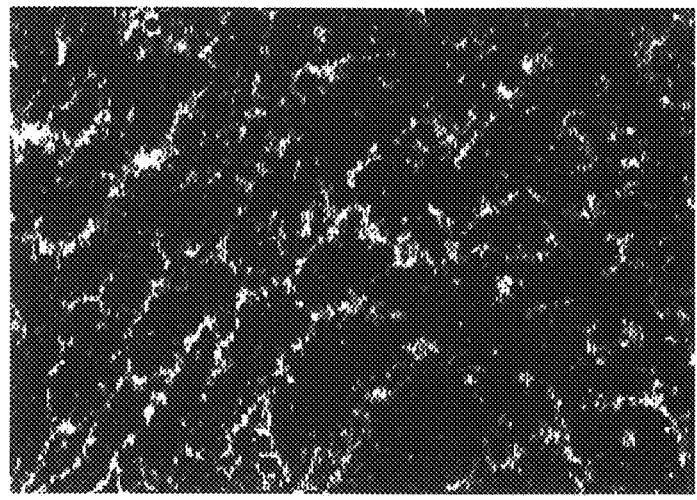

An image in which the numerical value of the likelihood of the blood vessel region obtained in this manner has been configured as the pixel value can be represented as a blood vessel extraction image. FIGS. 6(a) and 6(b) are diagrams illustrating an example of a captured image and a blood vessel extraction image obtained in the present embodiment. In the blood vessel extraction image illustrated in FIG. 6(b), the higher the numerical value of the likelihood of the blood vessel region in a region, the whiter the color displaying the region. In the captured image illustrated in FIG. 6(a), images of a thick blood vessel to a thin blood vessel appear. On the other hand, in the blood vessel extraction image illustrated in FIG. 6(b), a region where the numerical value of the likelihood of the blood vessel region is high (white) is represented at the same position as that of the image of the blood vessel in the captured image illustrated in FIG. 6(a). As described above, the position of the image of the blood vessel in the captured image and the position of the region in which the likelihood of the blood vessel region in the blood vessel extraction image is high substantially coincide with each other. From this, it can be seen that the blood vessel region is appropriately detected and digitized regardless of the thickness of the blood vessel, depending on the likelihood of the blood vessel region obtained in the present embodiment.

Therefore, the blood vessel feature amount calculation unit 224 can calculate the blood vessel feature amount by integrating the numerical values of the likelihood of the blood vessel region with each other in the entire image. The blood vessel feature amount is an amount representing a magnitude of an amount of blood vessels appearing in the biological tissue by a numerical value. It becomes easy for the blood vessel to appear on a surface of the biological tissue depending on a magnitude of such a blood vessel feature amount, such that it is possible to know that a mucous membrane becomes thin. In addition, it is possible to know that the biological tissue is in a stage before inflammation occurs.

Since the size of the template TP along the orthogonal direction orthogonal to the one direction is smaller than that of the template TP in the one direction, it is not necessary to prepare a plurality of templates TP in which the pattern shapes (the gray regions illustrated in FIGS. 5(a) to 5(e)) extend linearly in an inclined direction inclined with respect to the one direction and make repeated determinations using different templates TP. However, since a shape of the blood vessel does not extend linearly, but extends to be bent, curved, or inclined, it is also preferable to provide a plurality of pattern shapes similar to the shape of the blood vessel, from the viewpoint of obtaining the likelihood of the blood vessel region with high accuracy. In this case, it is preferable that the blood vessel region determination unit 222 is configured to calculate a maximum value of a plurality of approximation degrees indicating degrees of approximation to the pattern shapes as the likelihood of the blood vessel region, using the template (spatial filter) corresponding to each of the plurality of pattern shapes with respect to the pixel row extending in the one direction.

Note that in a case where the approximation degrees are obtained using the plurality of templates having the plurality of shapes, it is preferable from the viewpoint of obtaining approximation degrees to shapes of various blood vessels that the plurality of pattern shapes include a line shape extending in the orthogonal direction orthogonal to the one direction and an inclined shape extending at an inclination angle exceeding 0° and less than 90° with respect to the orthogonal direction.

A pixel value of the image used at the time of calculating the likelihood of such a blood vessel region is only required to be a pixel value regarding a color component that allows the blood vessel to be distinguishable from parts other than the blood vessel. For example, a pixel value of a color component may be a pixel value represented by a ratio of the pixel value of the color component to a pixel value of another color component or may be a luminance value of each pixel of an image (monotone image) represented by luminance.

According to the embodiment, it is preferable that an image of the biological tissue whose likelihood of the blood vessel region is obtained is a color component image in which information regarding an amount of a predetermined color component in the image of the biological tissue obtained by the electronic endoscope 100 is represented by a numerical value for each pixel. For example, the color component is a red component. In many cases, the blood vessel has a stronger degree of red color than a healthy part of the biological tissue and than an inflammatory part of the biological tissue, and can thus be distinguished from the healthy part and the inflammatory part.

A pixel value of a red component exhibited by a blood vessel is used as a pixel value of an image used at the time of calculating a likelihood of a blood vessel region, which will hereinafter be described in a second embodiment.

Second Embodiment

Figure 7A:
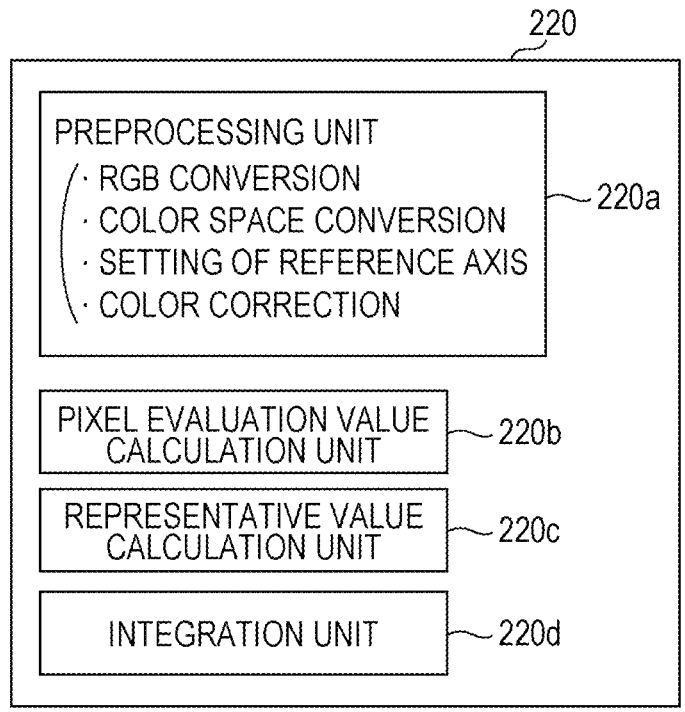
FIGS. 7(a) to 7(c) are diagrams illustrating an example of a configuration of an image processing unit that obtains a severity of a lesion part in the second embodiment.
Figure 7B:
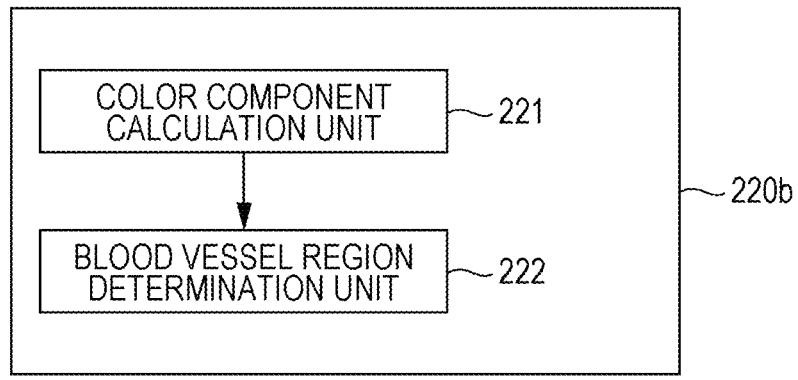
Figure 7C:
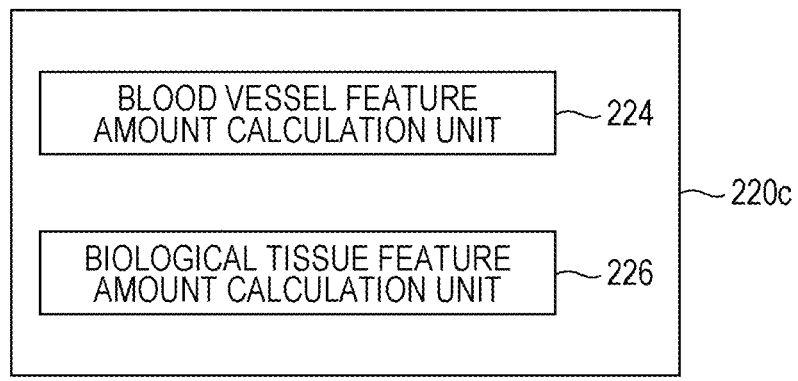

FIGS. 7(a) to 7(c) are diagrams for describing an example of main units of a configuration of an image processing unit 220 in a second embodiment that obtains a severity of a lesion part using a blood vessel feature amount indicating a feature of a blood vessel calculated by a blood vessel feature amount calculation unit 224 by a numerical value.

The image processing unit 220 is a portion that obtains a severity of a lesion obtained by digitizing a degree of lesion in the biological tissue from the image of the biological tissue obtained by the electronic endoscope 100. The image processing unit 220 includes a preprocessing unit 220a, a pixel evaluation value calculation unit 220b, a representative value calculation unit 220c, and an integration unit 220d.

The pixel evaluation value calculation unit 220b includes a color component calculation unit 221 in addition to the blood vessel region determination unit 222 described in the first embodiment. The color component calculation unit 221 obtains a redness representing a degree of red color by a numerical value, for each pixel. The calculation of the redness will be described later.

The color component calculation unit 221 of the pixel evaluation value calculation unit 220b calculates a biological tissue redness as a first pixel evaluation value by digitizing a degree of red color of the biological tissue for each pixel. The blood vessel region determination unit 222 calculates a numerical value of the likelihood of the blood vessel region using the template TP described in the first embodiment for a redness image configured with the first pixel evaluation value as a pixel value. The likelihood of the blood vessel region is obtained using the redness image, and is thus a blood vessel redness obtained by digitizing the degree of red color of the blood vessel region extending linearly on the biological tissue. That is, the blood vessel redness is a value obtained by digitizing both the likelihood of the blood vessel region and the degree of red color. The blood vessel region determination unit 222 calculates this value as a second pixel evaluation value.

The representative value calculation unit 220c includes a biological tissue feature amount calculation unit 226 in addition to the blood vessel feature amount calculation unit 224 described in the first embodiment. The biological tissue feature amount calculation unit 226 calculates a representative value of the biological tissue redness in the image. The calculation of this representative value will also be described later.

First, a description will be sequentially provided from the preprocessing unit 220a.

The preprocessing unit 220a is a portion that performs preprocessing on an image for evaluating a degree of red color indicated by the biological tissue. The preprocessing unit 220a performs each processing of RGB conversion, color space conversion, setting of a reference axis, and color correction, as illustrated as an example.

The preprocessing unit 220a converts the image signal (the luminance signal Y and the color difference signals Cb and Cr) input from the driver signal processing circuit 112 into image color components (R, G, and B) using predetermined matrix coefficients.

The preprocessing unit 220a further performs color space conversion in which image data converted into the image color components is orthogonally projected onto an RG plane. Specifically, image color components of each pixel of an RGB color space defined by three primary colors of R, G, and B are converted into image color components of R and G. Conceptually, the image color components of each pixel in the RGB color space are plotted in the RG plane (for example, a partition in the RG plane that takes a pixel value of an R component of 0 to 255 and a pixel value of a G component of 0 to 255) according to pixel values of R and G components. Hereinafter, for convenience of explanation, points of the image color components of each pixel of the RGB color space and points of the image color components plotted in an RG color space are referred to as "pixel corresponding points". The image color components of each of R, G, and B of the RGB color space are, for example, color components having a wavelength of 620 to 750 nm, a wavelength of 495 to 570 nm, and a wavelength of 450 to 495 nm, respectively. The color components constitute a color space (including a color plane). Hue and saturation are excluded from the "color components".

In the preprocessing unit 220a, a reference axis in the RG plane necessary for evaluating the biological tissue redness and the blood vessel redness is set.

In a biological tissue in a body cavity of a patient, which is an object, an R component of image color components is dominant over the other components (G component and B component) due to an influence of a hemoglobin pigment and the like. In a case where a degree of lesion in a lesion part is low and the lesion part is an inflammatory part, the stronger the inflammation, the stronger the red color (R component) than the other colors (G component and B component). However, a color of a captured image in the body cavity changes depending on an imaging condition (for example, a shining state of illumination light) that affects brightness. Illustratively, a shaded portion that the illumination light does not reach becomes black (which is an achromatic color, and, for example, values of the image color components of R, G, and B are zero or a value close to zero), and a portion on which the illumination light shines strongly and which regularly reflects the illumination light becomes white (which is an achromatic color, and, for example, in a case where values of the image color components of R, G, and B are 8-bit gradation, they are 255 or a value close to 255).

That is, even in a case where an image of the same inflammatory part where inflammation is occurring is captured, the stronger the illumination light shining on the inflammatory part, the larger the pixel value of the inflammatory part. For that reason, depending on the shining state of the illumination light, the color component of the image may take a value that does not correlate with a strength of the inflammation.

In general, a healthy part within the body cavity where the inflammation is not occurring is covered with a sufficient mucous membrane. On the other hand, the inflammatory part in the body cavity where inflammation is occurring is not covered with a sufficient mucous membrane. Specifically, since blood and body fluids leak from the blood vessel simultaneously with dilation of the blood vessel, the mucous membrane becomes relatively thin, such that a color of the blood becomes easily visible. The mucous membrane is basically white, but is slightly yellowish, and a color (yellow) that appears on the image changes depending on a shade of the mucous membrane (thickness of the mucous membrane). Therefore, the shade of the mucous membrane is also considered to be one of indexes for evaluating a degree of inflammation.

Figure 8:
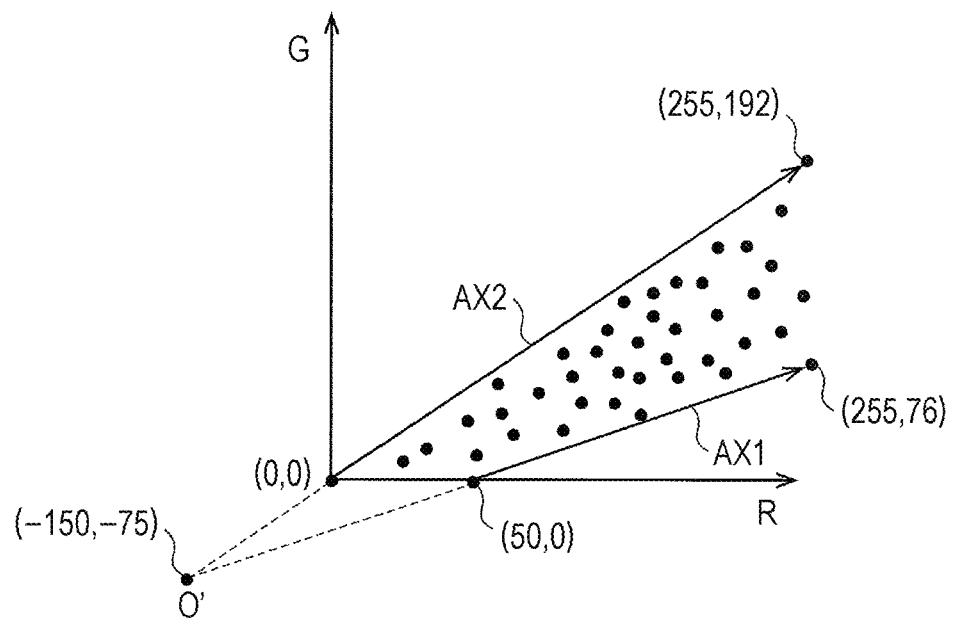
FIG. 8 is a diagram illustrating an example of reference axes in a color space used in the second embodiment.

Therefore, as illustrated in FIG. 8, in the RG color space, a straight line passing through (50, 0) and (255, 76) is set as one of reference axes, and a straight line passing through (0, 0) and (255, 192) is set as one of the reference axes. For convenience of explanation, the former reference axis is referred to as a "hemoglobin change axis AX1", and the latter reference axis is referred to as a "mucous membrane change axis AX2". FIG. 8 is a diagram illustrating an example of reference axes in a color space used in the second embodiment.

Plots illustrated in FIG. 8 are obtained as a result of analyzing a large number of reference images of the biological tissue in the body cavity. The reference images used for the analysis include inflammation image examples at each stage such as an inflammation image example with the highest degree of inflammation (inflammation image example of the most severe level), an inflammation image example with the lowest degree of inflammation (image example considered to be a substantially healthy part), or the like. In the example illustrated in FIG. 8, only some of the plots obtained as a result of the analysis are illustrated for convenience of clarifying the drawing. The number of plots actually obtained as a result of the analysis is much larger than the number of plots illustrated in FIG. 8.

As described above, the stronger the inflammation of the part, the stronger the R component of the color components of the image becomes than the other components (G component and B component). For that reason, an axis on a boundary line between a region where the plots are distributed and a region where the plots are not distributed and a boundary line closer to an R axis than a G axis, that is, an axis on a boundary line passing through (50, 0) and (255, 76) in the example illustrated in FIG. 8 is set as an axis having a high correlation with a part with the strongest degree of inflammation, that is, a part with the highest degree of inflammation. This axis is the hemoglobin change axis AX1.

On the hemoglobin change axis AX1, plots corresponding to the inflammatory part with the highest degree of inflammation whose image is captured in various imaging conditions, for example, a shining state of illumination light, are superimposed. Therefore, the hemoglobin change axis AX1 is an axis on which the plotted pixel corresponding points converge as the degree of inflammation of the biological tissue becomes higher.

On the other hand, the closer the biological tissue is to the healthy part, the stronger the G component (or the B component) of the color components of the image is than the R component. For that reason, an axis on a boundary line between a region where the plots are distributed and a region where the plots are not distributed and a boundary line closer to the G axis than the R axis, that is, an axis on a boundary line passing through (0, 0) and (255, 192) in the example illustrated in FIG. 8 is set as an axis having a high correlation with a part with the lowest degree of inflammation, that is, a part with the lowest degree of inflammation and a part considered to be a substantially healthy part. This axis is the mucous membrane change axis AX2. On the mucous membrane change axis AX2, plots corresponding to the part with the lowest degree of inflammation whose image is captured in various imaging conditions, for example, a shining state of illumination light, that is, the part considered to be a substantially normal part, are superimposed. Therefore, the mucous membrane change axis AX2 is an axis on which the plotted pixel corresponding points converge as the degree of inflammation becomes lower (closer to the healthy part).

Supplementally, a part with the highest degree of lesion in the lesion part is accompanied by bleeding. On the other hand, a part with the lowest degree of lesion is a substantially normal healthy part, and is thus covered with a sufficient mucous membrane. For that reason, it can be grasped that the plots in the RG color space illustrated in FIG. 8 are distributed within a region sandwiched between an axis with the highest correlation with a color of blood (hemoglobin pigment) and an axis with the highest correlation with a color of the mucous membrane. For that reason, a boundary line close to the R axis (whose R component is strong), of the boundary lines between the region where the plots are distributed and the region where the plots are not distributed corresponds to the axis (hemoglobin change axis AX1) indicating the inflammatory part with the highest degree of inflammation, and a boundary line close to the G axis (whose G component is strong) of the boundary lines described above corresponds to the axis (mucous membrane change axis AX2) indicating the inflammatory part with the lowest degree of inflammation.

After the setting of the reference axes is performed as described above, processing for calculating a biological tissue redness indicating a degree of red color to be described later is performed on color components of an orthogonally projected image. Before the processing for calculating the biological tissue redness, color correction is performed on orthogonally projected pixel data.

The reference axes illustrated in FIG. 8 are an example, and the reference axes vary depending on a type of disease.

The preprocessing unit 220a performs color correction on the color components of the image represented in the RG color space before calculating an inflammation evaluation value. Correction matrix coefficients are stored in a memory (not illustrated). In order to prevent inflammation evaluation values to be described later from varying when images are captured by different electronic endoscope systems in spite of the same inflammatory part (in other words, in order to suppress inter-individual errors of electronic scopes), the preprocessing unit 220a corrects pixel data (R,G), which are pixel corresponding points in the RG color space of each pixel, as represented in the following Equation, using the correction matrix coefficients.

$$\begin{pmatrix} R_{new} \\ G_{new} \end{pmatrix} = \begin{pmatrix} M_{00} & M_{01} \\ M_{10} & M_{11} \end{pmatrix} \begin{pmatrix} R \\ G \end{pmatrix}$$

Figure 9:
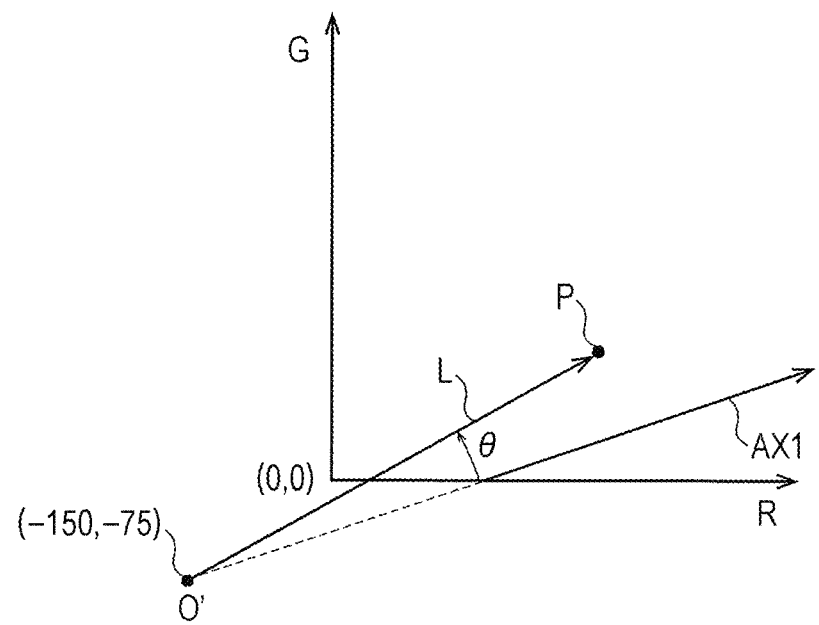
FIG. 9 is a diagram for describing a method of calculating a deviation angle for calculating a biological tissue redness used in the second embodiment.

$R_{new}$: Pixel data (R component) after being corrected
$G_{new}$: Pixel data (G component) after being corrected
$M_{00}$ to $M_{11}$: Correction matrix coefficient
R: Pixel data (R component) before being corrected
G: Pixel data (G component) before being corrected The color component calculation unit 221 of the pixel evaluation value calculation unit 220b selects one pixel of interest among the pixels, and calculates a deviation angle for calculating a biological tissue redness for the selected pixel of interest on the basis of information of a color component of the pixel of interest. That is, digitization processing for digitizing a degree of red color of the biological tissue on the basis of the information of the color component of the pixel is performed. The biological tissue redness is a value indicating the degree of inflammation as described later. FIG. 9 is a diagram for describing a method of calculating a deviation angle for calculating the biological tissue redness used in the second embodiment. Specifically, the color component calculation unit 221 sets an intersection point between the hemoglobin change axis AX1 and the mucous membrane change axis AX2 as a reference point O', and calculates a deviation angle θ at which a direction of a line segment L connecting the reference point O' and a pixel corresponding point P of the pixel of interest to each other deviates from the hemoglobin change axis AX1, as illustrated in FIG. 9. Note that the reference point O' is located at coordinates (−150, −75). An example in which the reference point O' is set to the coordinates (−150, −75) has been taken, but the present disclosure is not limited thereto. The reference point O' can be appropriately changed, and may be, for example, an intersection point between the R axis and the G axis in the RG color space.

A suitable coordinate position as the reference point O' is, for example, a position where an error of an evaluation result due to a fluctuation in brightness can be reduced. Specifically, it is preferable that the reference point O' is set by obtaining, in advance, a point that minimizes an error between an evaluation result in a dark part (whose luminance is less than a predetermined value) and an evaluation result in a non-dark part (whose luminance is the predetermined value or more).

In addition, for example, if the reference point O' is set between coordinates (−10, −10) and (10, 10), a change amount in the angle θ in a case where the pixel corresponding point changes becomes large as compared with a case of setting the coordinates (−150, −75) and the like as the reference point O', and a resolution is thus improved. Therefore, an evaluation result with high accuracy can be obtained.

On the other hand, by setting the reference point O' between coordinates (−50, −50) and (−200, −200), an evaluation result indicating the degree of inflammation is hardly affected by noise.

If brightness of a captured image of the biological tissue in the body cavity changes depending on a shining state of white light, a color of the image is affected by an individual difference, an imaging place, a state of inflammation, or the like, but in the RG color space, generally, the color of the image changes along the hemoglobin change axis AX1 in an inflammatory part with the highest severity and changes along the mucous membrane change axis AX2 in an inflammatory part with the lowest degree of inflammation. In addition, it is estimated that a color of an image at an inflammatory part where the degree of inflammation is an intermediate degree changes with the same tendency. That is, if the brightness of the image changes depending on the shining state of the illumination light, a pixel corresponding point corresponding to the inflammatory part shifts in an azimuth direction with the reference point O' as a starting point. In other words, if the brightness of the image changes depending on the shining state of the illumination light, the pixel corresponding point corresponding to the inflammatory part moves while the deviation angle θ with respect to the mucous membrane change axis AX2 is kept constant, such that a distance between the reference point O' and the pixel corresponding point changes. This means that the deviation angle θ is a parameter that is not substantially affected by the change in the brightness of the image.

The smaller the deviation angle θ, the stronger the R component than the G component, which indicates that the degree of red color in the lesion part is relatively large. In addition, the larger the deviation angle θ, the stronger the G component than the R component, which indicates that the degree of red color is relatively small. Therefore, the color component calculation unit 221 normalizes the deviation angle θ so that the value becomes 255 when the deviation angle θ is zero and the value becomes zero when the deviation angle θ is θMAX. Note that θMAX is equal to an angle formed by the hemoglobin change axis AX1 and the mucous membrane change axis AX2. That is, the color component calculation unit 221 calculates a biological tissue redness falling within a range of 0 to 255 as a first pixel evaluation value, for each pixel of interest, by performing digitization processing for digitizing the degree of red color on the basis of information of the color component of each pixel of interest.

Note that the pixel of interest is selected one by one for all the pixels of the image.

Note that in the example illustrated in FIG. 9, the RG color space is used as the color space, but an RB color space can be used instead of the RG color space.

The color component calculation unit 221 further creates a color map image in which the image of the biological tissue is mosaicked with a display color that changes according to the biological tissue redness. In order to make it possible to display the color map image, a table in which biological tissue rednesses and predetermined display colors are associated with each other is stored in a storage area such as a memory (not illustrated) or the like. In this table, for example, different display colors are associated at an interval of 5. Illustratively, a blue color is associated in the range in which a pixel evaluation value is 0 to 5, different display colors are associated according to the order of colors in a hue circle each time the pixel evaluation value increases by 5, and a degree of red color is associated in the range in which the pixel evaluation value is 250 to 255.

It is assumed that the display color is a color that approaches a warm color from a cold color, for example, approaches a yellow color, and furthermore, a red color from a blue color as the biological tissue redness becomes larger. The color component calculation unit 221 determines the display color of the selected pixel of interest on the color map image according to the biological tissue redness of the pixel of interest with reference to the above table.

In this manner, the color component calculation unit 221 creates the color map image in which colors are given according to the biological tissue redness.

The blood vessel region determination unit 222 uses a redness image with the biological tissue redness calculated by the color component calculation unit 221 as a pixel value, that is, a redness image (color component image) configured with the first pixel evaluation value as a pixel value, as an image for obtaining a numerical value of the likelihood of the blood vessel region to calculate the likelihood of the blood vessel region appearing in an image of the biological tissue in the redness image as the second pixel evaluation value, that is, calculate the second pixel evaluation value representing the likelihood of the blood vessel region by a numerical value for each pixel. The likelihood of the blood vessel region is a value obtained using the redness image, and is thus a blood vessel redness indicating the redness of the blood vessel region.

The blood vessel region determination unit 222 extracts the blood vessel region by the obtained likelihood, if necessary. Specifically, the approximation degrees to the pattern shapes are calculated using the templates TP1 to TP5 long in the one direction that have been described in the first embodiment for the redness image (image with the biological tissue redness as the pixel value), and the numerical value of the likelihood of the blood vessel region in the redness image is calculated as the second pixel evaluation value.

Such a second pixel evaluation value is obtained using the redness image, and is thus a pixel value including information of the biological tissue redness and information of the likelihood of the blood vessel region. Therefore, the blood vessel region determination unit 222 can extract the blood vessel region by determining whether or not a value of the likelihood of the blood vessel region in each pixel is larger than a predetermined value and determining that the pixel is the blood vessel region in a case where the value of the likelihood of the blood vessel region in the pixel is larger than the predetermined value.

Note that the blood vessel region determination unit 222 may obtain the blood vessel redness by obtaining the likelihood of the blood vessel region using an image other than the redness image, in addition to a case where the blood vessel redness is obtained by using the redness image. In this case, a value may be obtained by normalizing the likelihood of the blood vessel region in the range of 0 to 1 and a result of performing correction so that the higher the value, the higher the likelihood of the blood vessel region and the lower the value, the lower the likelihood of the blood vessel region may be calculated as the value of the likelihood of the blood vessel region. In this case, a result of multiplying a value of the biological tissue redness in each pixel calculated by the color component calculation unit 221 by the value of the likelihood of the blood vessel region in the corresponding pixel may be obtained as the second pixel evaluation value, which is the blood vessel redness.

The biological tissue feature amount calculation unit 226 calculates the representative value of the biological tissue redness of the biological tissue whose image is captured as a first representative evaluation value by integrating the first pixel evaluation values, which are the biological tissue rednesses of each pixel calculated by the color component calculation unit 221, with each other. That is, the biological tissue feature amount calculation unit 226 calculates the first representative evaluation value regarding a feature of the biological tissue by integrating the first pixel evaluation values of each pixel in the redness image with each other.

The blood vessel feature amount calculation unit 224 calculates a representative value of the blood vessel redness as a second representative evaluation value by integrating the second pixel evaluation values, which are the blood vessel rednesses of each pixel, with each other. That is, the blood vessel feature amount calculation unit 224 calculates the blood vessel feature amount indicating the feature of blood vessel as the second representative evaluation value in the blood vessel region by integrating the second pixel evaluation values, which are numerical values of the likelihood of the blood vessel region, with each other in the entire redness image.

The integration processing may be averaging processing for calculating an average value of the biological tissue rednesses and the blood vessel rednesses of each pixel or may be another known processing, for example, processing for obtaining a median value. The averaging processing includes processing for obtaining a simple average value and processing for obtaining a weighted average value. In addition, the known processing may be processing for dividing each of the biological tissue redness and the blood vessel redness into at least two or more ranked levels and calculating the representative value by substituting a total value P of values obtained by multiplying the number of pixels belonging to each level by a predetermined weighting coefficient into a predetermined equation. In this case, the predetermined equation is, for example, $1/(1+e^{-P})$. In this case, it is preferable that the weighting coefficient is a coefficient obtained by a multiple logistic regression analysis so as to have a correlation with a subjective evaluation result by a doctor.

The integration unit 220d calculates a severity of the lesion by integrating the first representative evaluation value, which is the representative value of the biological tissue redness, and the second representative evaluation value, which is the representative value of the blood vessel redness, with each other. The integration between the first representative evaluation value and the second representative evaluation value is performed by calculation such as addition of the second representative evaluation value to the first representative evaluation value, subtraction of the second representative evaluation value from the first representative evaluation value, or the like. For example, when the second representative evaluation value is equal to or higher than a predetermined threshold value, the severity is defined as a result of subtracting the second representative evaluation value from the first representative evaluation value, and when the second representative evaluation value is lower than the predetermined threshold value, the severity is defined as a result of adding the second representative evaluation value to the first representative evaluation value.

The integration unit 220d generates a signal for displaying the calculated severity together with the color map image created by the pixel evaluation value calculation unit 220b on a screen, and sends the generated signal to the monitor 300.

Figure 10:
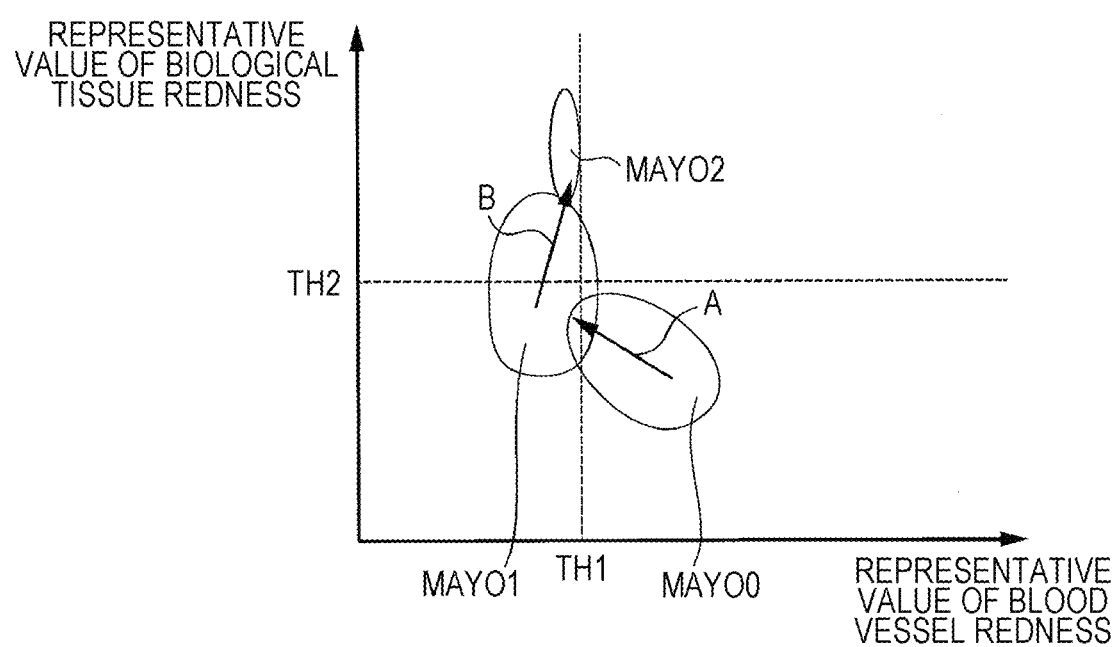
FIG. 10 is a diagram schematically illustrating a distribution range of doctor's subjective evaluation results for images of a lesion part of ulcerative colitis.

FIG. 10 is a diagram schematically illustrating a distribution range of MAYO endoscopic subscores, which are doctor's subjective evaluation results for hundred images of a lesion part of ulcerative colitis. The severity becomes higher from MAYO0 toward MAYO2. In FIG. 10, the distribution range of the MAYO endoscopic subscores is illustrated on a Cartesian coordinate system of the representative value of the biological tissue redness and the representative value of the blood vessel redness. Each of MAYO0, MAYO1, and MAYO2 in FIG. 10 indicates that the MAYO endoscopic subscore is 0, 1, and 2. The progress from MAYO0 to MAYO2 means that the severity of the lesion becomes higher.

As can be seen from FIG. 10, in a case of proceeding from MAYO0 to MAYO1, it schematically indicates that the blood vessel redness decreases and the biological tissue redness increases. In addition, in a case of proceeding from MAYO1 to MAYO2, it schematically indicates that both the blood vessel redness and the biological tissue redness increase.

Therefore, it can be seen from this fact that it is preferable in terms of corresponding to the MAYO endoscopic subscore to make a method of calculating the severity differ depending on whether the representative value of the blood vessel redness, which is the second representative evaluation value, is equal to or higher than or is less than a predetermined threshold value.

Note that the blood vessel feature amount calculation unit 224 performs processing for integrating the second pixel evaluation values, which are the blood vessel rednesses, with each other for all pixels, but is not limited to this integration. For example, the blood vessel feature amount calculation unit 224 may compare the second pixel evaluation value with a threshold value, extract pixels having the second pixel evaluation value equal to or higher than the threshold value as the blood vessel region, and integrate the second pixel evaluation values, which are the blood vessel rednesses, with each other in the extracted region.

Figure 11:
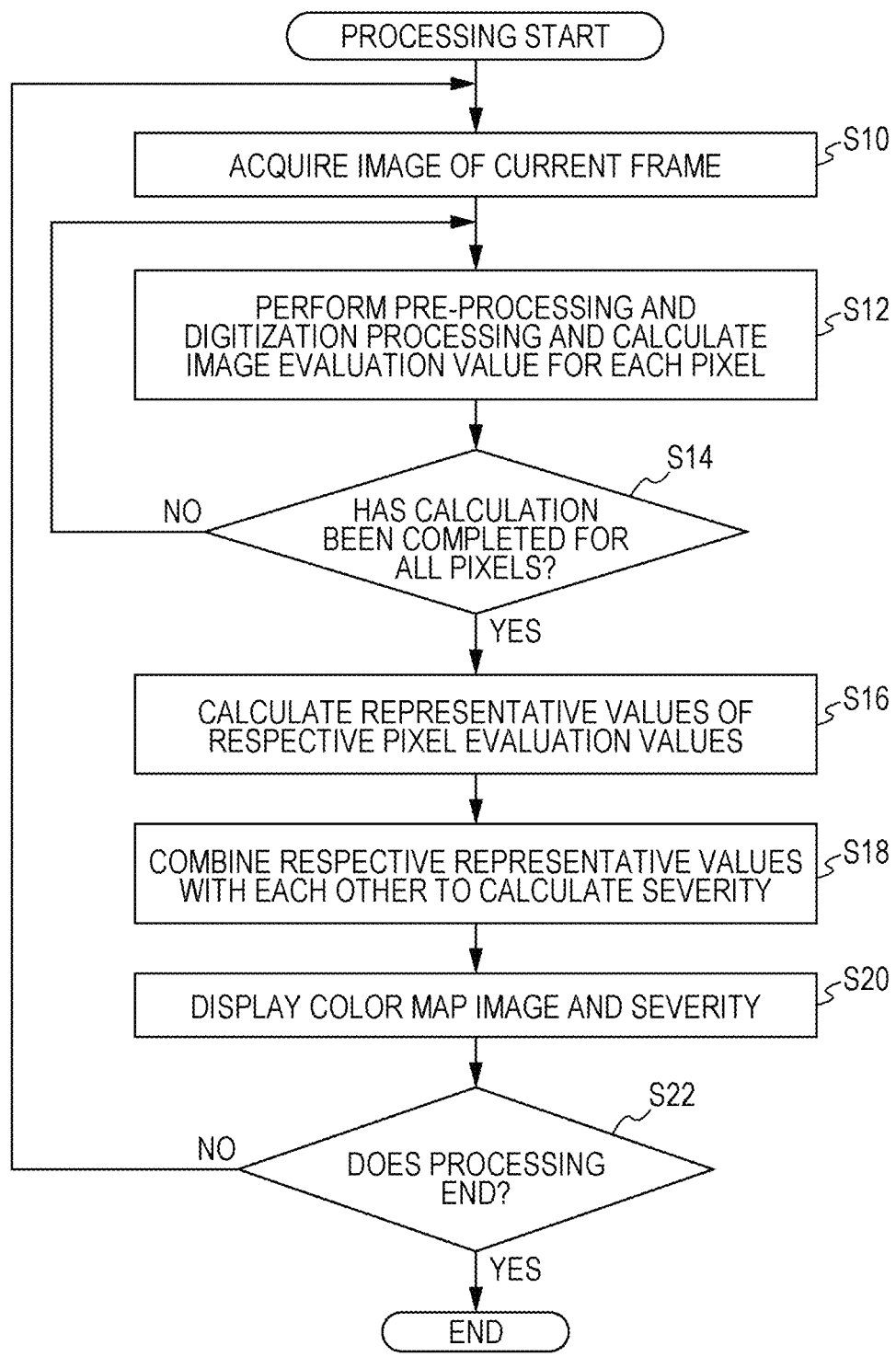
FIG. 11 is a diagram illustrating an example of a flow of processing for calculating a severity of a lesion by a processor for an electronic endoscope according to the second embodiment.

The processor 200 for an electronic endoscope including such an image processing unit 220 calculates the severity of the lesion according to a flow illustrated in FIG. 11 and displays the severity on the monitor 300. FIG. 11 is a diagram illustrating an example of a flow of processing for calculating the severity of the lesion by the processor 200 for an electronic endoscope according to the second embodiment.

First, the image processing unit 220 acquires an image of a current frame (step S10).

Next, the preprocessing unit 220a performs preprocessing including the RGB conversion, the color space conversion, the setting of the reference axis, and the color correction described above, and tone enhancement processing if necessary, and the pixel evaluation value calculation unit 220b calculates the first pixel evaluation value and the second pixel evaluation value, for example, the biological tissue redness and the blood vessel redness, for each pixel, for the image on which the preprocessing has been performed (step S12).

The pixel evaluation value calculation unit 220b determines whether or not the pixel evaluation values have been calculated for all the pixels of the image of the current frame (step S14). In a case where the calculation of the pixel evaluation values has completed for all the pixels, the representative value calculation unit 220c calculates the first representative evaluation value and the second representative evaluation value by integrating the pixel evaluation values with each other (step S16). The representative value is calculated for each of the first pixel evaluation value and the second pixel evaluation value.

Subsequently, the integration unit 220d combines the representative values with each other to calculate one severity (step S18). That is, one numerical value obtained by calculating and integrating the representative values with each other is calculated as the severity of the lesion.

Finally, the integration unit 220d displays the calculated severity and the color map image in which the image of the biological tissue is mosaicked with the display color that changes according to the biological tissue redness, on the monitor 300 (step S20).

Figure 12:
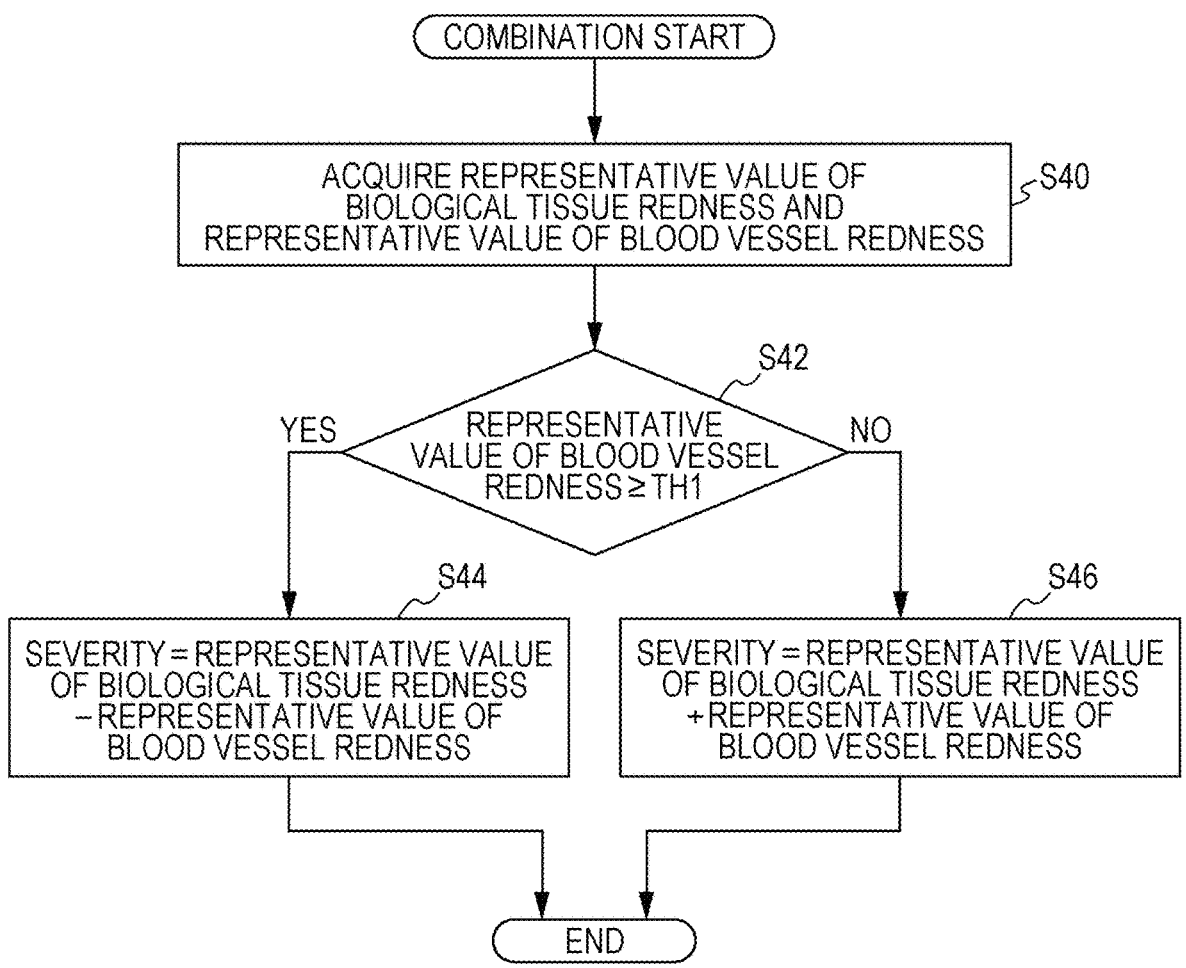
FIG. 12 is a diagram for describing an example of a flow of a method of combining representative values with each other performed in the second embodiment.

FIG. 12 is a diagram for describing an example of a flow of a method of combining the representative values with each other. The integration unit 220*d* acquires the representative value of the biological tissue redness and the representative value of the blood vessel redness calculated by the representative value calculation unit 220*c* (step S40). The integration unit 220*d* determines whether or not the representative value of the blood vessel redness is equal to or higher than a predetermined threshold value TH1 (see FIG. 10) (step S42). In a case where the representative value of the blood vessel redness is equal to or higher than the predetermined threshold value TH1, the integration unit 220*d* subtracts the representative value of the blood vessel redness from the representative value of the biological tissue redness, and sets this subtraction result as the severity (step S44). Note that as for the subtraction, a value obtained by multiplying the representative value of the blood vessel redness by a constant β may be subtracted from a value obtained by multiplying the representative value of the biological tissue redness by a constant α.

On the other hand, in a case where the representative value of the blood vessel redness is less than the predetermined threshold value TH1, the integration unit 220*d* adds the representative value of the blood vessel redness to the representative value of the biological tissue redness, and sets this addition result as the severity (step S46). Note that as for the addition, a value obtained by multiplying the representative value of the blood vessel redness by a constant β may be added to a value obtained by multiplying the representative value of the biological tissue redness by a constant α.

Instead of the threshold value TH1 for comparing with the representative value of the blood vessel redness, a threshold value TH2 (see FIG. 10) for comparing with the representative value of the biological tissue redness may be used.

Figure 5:
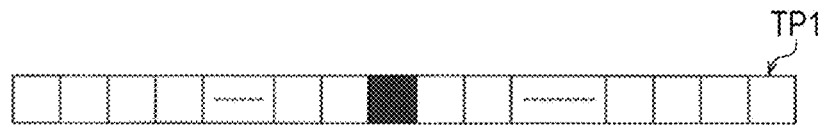
FIGS. 5(a) to 5(e) are diagrams illustrating examples of templates (spatial filters) used in the first embodiment and the second embodiment.
Figure 5:
Figure 5:
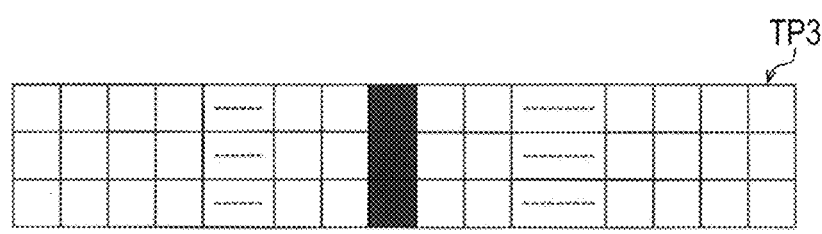
Figure 5:
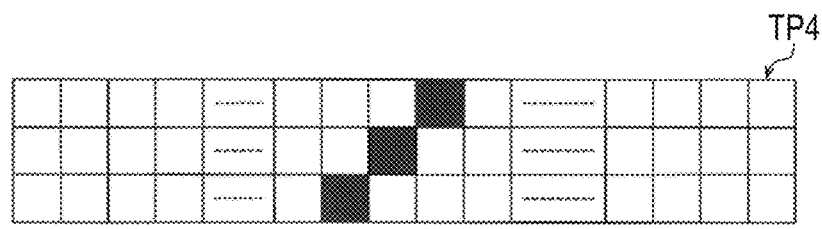
Figure 5:
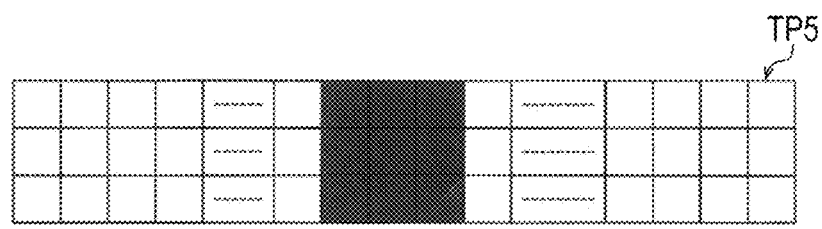

As described above, in the second embodiment, the templates TP1 to TP5 illustrated in FIGS. 5(*a*) to 5(*e*) are used for the redness image to calculate the value of the likelihood of the blood vessel region. Therefore, a blood vessel redness with high accuracy can be obtained, and the severity of the lesion part with high accuracy can be calculated using this blood vessel redness.

In a case where the color components of the image include the red component, the green component, and the blue component, the color component calculation unit 221 is configured to calculate the first pixel evaluation value, which is the biological tissue redness, on the basis of the deviation angle θ at which the direction of the line segment connecting the reference point set in the color space and the pixel corresponding point corresponding to the color component of each pixel of the image to each other deviates from the predetermined reference axis (hemoglobin change axis AX1) in the color space defined by the red component and the blue component (or the green component), as illustrated in FIG. 9, and can thus accurately obtain the degree of the red component even in the image captured in the various imaging conditions, for example, the shining state of the illumination light. For this reason, the severity of the lesion part can be accurately calculated using the blood vessel redness and the biological tissue redness.

The endoscope system according to the present invention has been described in detail hereinabove, but the endoscope system according to the present invention is not limited to the above-described embodiment, and may of course be modified or altered in various ways in a range not deviating from the scope and spirit of the present invention.

REFERENCE SIGNS LIST

1 Electronic endoscope system
100 Electronic endoscope
200 Processor for electronic endoscope
220 Image processing unit
220*a* Preprocessing unit
220*b* Pixel evaluation value calculation unit
220*c* Representative value calculation unit
220*d* Integration unit
221 Color component calculation unit
222 Blood vessel region determination unit
224 Blood vessel feature amount calculation unit
226 Biological tissue feature amount calculation unit
230 Light source unit
300 Monitor
400 Printer
600 Server

The invention claimed is:

1. An endoscope system comprising:
an electronic endoscope configured to capture an image of a biological tissue; and
a processor that includes an image processing unit including: a blood vessel region determination unit configured to obtain a likelihood of a blood vessel region appearing in the image of the biological tissue as a numerical value on the basis of a shape characterizing a blood vessel, for each of a plurality of parts of the image of the biological tissue, from the image of the biological tissue obtained by the electronic endoscope; and a blood vessel feature amount calculation unit configured to calculate a blood vessel feature amount indicating a feature amount of the blood vessel region by integrating the numerical values of the likelihood of the blood vessel region with each other in the entire image,
wherein the blood vessel region determination unit is configured to calculate an approximation degree as the likelihood of the blood vessel region, for each pixel of the image, using a spatial filter with respect to a pixel row of at least one stage of the image extracted along one direction of array directions of pixels of the image, the approximation degree representing a degree of approximation to a pattern shape that approximates to a blood vessel shape, by a numerical value, and the spatial filter being composed of a plurality of pixels whose pixel values are represented so as to correspond to the pattern shape, and
a size of the spatial filter along the one direction is larger than that of the spatial filter along an orthogonal direction orthogonal to the one direction,
wherein a ratio of a dimension of the spatial filter in the one direction to a dimension of the spatial filter in the orthogonal direction is 20 to 100.

2. The endoscope system according to claim 1, wherein the blood vessel region determination unit associates pixels of an examination target area of the pixel row with respective pixels of the spatial filter, and obtains the approximation degree on the basis of a total value of values obtained by multiplying pixel values of the pixels of the examination target area by pixel values of corresponding pixels of the spatial filter.

3. The endoscope system according to claim 1, wherein the spatial filter is provided so as to correspond to each of a plurality of pattern shapes, and the blood vessel region determination unit is configured to calculate a maximum value of a plurality of approximation degrees obtained using the spatial filter corresponding to each of the plurality of pattern shapes as the likelihood of the blood vessel region.

4. The endoscope system according to claim 3, wherein the plurality of pattern shapes include a linear shape extending in the orthogonal direction and an inclined shape extending at an inclination angle exceeding 0° and less than 90° with respect to the orthogonal direction.

5. The endoscope system according to claim 1, wherein an image of the biological tissue used at the time of obtaining the likelihood of the blood vessel region of the biological tissue is a color component image in which information regarding an amount of a predetermined color component in the image of the biological tissue obtained by the electronic endoscope is represented by a numerical value for each pixel.

6. The endoscope system according to claim 1, wherein the image processing unit includes:

a pixel evaluation value calculation unit including: a color component calculation unit configured to calculate a first pixel evaluation value, for each pixel, the first pixel evaluation value being a pixel evaluation value capable of distinguishing a feature of an appearance appearing in a lesion part of the biological tissue from a feature of an appearance of a healthy part of the biological tissue by a color component indicated by the lesion part and indicating a degree of the feature regarding the color component indicated by the lesion part; and the blood vessel region determination unit, the blood vessel region determination unit is configured to calculate a second pixel evaluation value, for each pixel, using a color component image configured with the first pixel evaluation value calculated by the color component calculation unit as a pixel value as an image for obtaining the numerical value of the likelihood of the blood vessel region, the second pixel evaluation value representing the likelihood of the blood vessel region by a numerical value, and the image processing unit further includes:

a representative value calculation unit including: the blood vessel feature amount calculation unit configured to calculate the blood vessel feature amount as a second representative evaluation value in the blood vessel region by integrating the second pixel evaluation values with each other in the entire color component image, the second pixel evaluation values being numerical values of the likelihood of the blood vessel region; and a biological tissue feature amount calculation unit configured to calculate a first representative evaluation value of the feature of the biological tissue by integrating the first pixel evaluation values of each pixel in the color component image with each other; and an integration unit configured to calculate one numerical value obtained by calculating and integrating the first representative evaluation value and the second representative evaluation value with each other, as a severity of a lesion of the lesion part.

7. The endoscope system according to claim 6, wherein a degree of the feature of the appearance is a degree of inflammation of the biological tissue, and the color component is a red component.

8. The endoscope system according to claim 6, wherein the color component of the image includes a red component, a green component, and a blue component, and the color component calculation unit is configured to calculate the first pixel evaluation value on the basis of a deviation angle at which a direction of a line segment connecting a reference point set in a color space and a pixel corresponding point corresponding to a color component of each pixel of the image to each other deviates from a predetermined reference axis passing through the reference point, the color space being defined by the red component and the blue component or the green component.

* * * * *